United States Patent [19]

Keese et al.

[11] 4,181,501

[45] Jan. 1, 1980

[54] METHOD AND APPARATUS FOR MEASURING ANTIBODY LEVELS

[75] Inventors: Charles R. Keese, Schoharie; Ivar Giaever; William J. Ward, III, both of Schenectady, all of N.Y.

[73] Assignee: General Electric Company, Schenectady, N.Y.

[21] Appl. No.: 23,695

[22] Filed: Mar. 26, 1979

[51] Int. Cl.$^2$ ............................................. G01N 33/16
[52] U.S. Cl. .................................. 23/230 B; 422/57; 422/58; 422/102; 424/12; 435/7
[58] Field of Search .................. 23/230 B; 422/57, 58, 422/102; 424/12; 195/127

[56] References Cited

U.S. PATENT DOCUMENTS

| | | | |
|---|---|---|---|
| 3,672,845 | 6/1972 | Verbeck | 422/57 |
| 3,692,486 | 9/1972 | Glenn | 23/230 B |
| 3,725,004 | 4/1973 | Johnson | 422/102 X |
| 3,884,641 | 5/1975 | Kraffczyk | 422/58 X |
| 3,960,489 | 6/1976 | Giaever | 23/230 B |
| 3,993,451 | 11/1976 | Verbeck | 422/57 |
| 4,018,662 | 4/1977 | Ruhenstroth-Bauer | 422/58 X |
| 4,054,490 | 10/1977 | Vesterberg | 195/127 X |
| 4,067,959 | 1/1978 | Bolz | 422/57 X |
| 4,147,752 | 4/1979 | Suovaniemi | 422/57 |

OTHER PUBLICATIONS

Hubert, T. S. Britton, "Hydrogen Ions", vol. I, 339–342, D. Van Nostrand, New York, 1943.

*Primary Examiner*—Sidney Marantz
*Attorney, Agent, or Firm*—Leo I. MaLossi; Joseph T. Cohen

[57] ABSTRACT

A diagnostic device is described employing a solid, rigid diagnostic substrate (having as a part thereof an exposed layer of first immunologically reactive biological particles) in combination with means spaced therefrom for containing a solution of second immunologically reactive biological particles specific to the first particles. Preferably these elements are arranged with the layer of first immunologically reactive biological particles on a glass slide having a metallized surface and facing the containing means with spacing therebetween. This spacing defines a wedge-shaped volume for containing test fluid. With a test fluid in place, after allowing diffusion to occur for a predetermined period of time, the extent of formation of a layer of the second particles (i.e., a second layer) on the first layer is determined. If such a second layer develops, this determination can be related to the concentration of first particles in the test fluid. Presence of the second layer is visible with good contrast to the unaided eye.

21 Claims, 3 Drawing Figures

METHOD AND APPARATUS FOR MEASURING ANTIBODY LEVELS

BACKGROUND OF THE INVENTION

This invention relates to a method and apparatus for determining the concentration of specifically interacting (e.g., immunologically reactive) biological particles in a specimen and, in particular, for quantitatively determining the antibody levels in human serum.

Immunological reactions are highly specific biochemical reactions in which a first immunologically reactive biological particle (e.g., protein, such as an antibody) combines, or links, with a second biological particle specific to the first. Immunological reactions taking place within a biological system, such as an animal or human being, are vital in combatting disease. In a biological system the entry of a foreign immunologically active particle (i.e., an antigen) causes the biological system to produce the specific antibody proteins to the antigen in a process not fully understood at this time. The antibody protein molecule has available chemical combining or binding sites, which complement those of the particle to which it is specific, so that these particles link or bond to form immunologically complexed particles.

Because antibodies are produced by biological systems in response to invasions thereof by foreign matter the detection of antibodies in a biological system is of medical diagnostic value in determining the antigens to which the system has been exposed. Each of the five major classes of antibodies (immunoglobulines IgG, IgM, IgA, IgE, and IgD) is apparently characterized by at least two heavy (long) peptide chains of amino acids and at least two light (short) peptide chains of the amino acids wherein the bond between the amino acids units is known as a peptide bond.

In order to perform such diagnostic tests, the appropriate protein of the immunologically reacting pair must be obtained. The only common source of an antibody protein is a living biological system. More particularly, only vertebrates are known at this time to exhibit immunological reactions to the introduction of a foreign protein or particle. It is known in the immunological art that antibody molecules function as antigens when introduced into the system of a vertebrate to which they are foreign proteins. Accordingly, specifically reacting anti-antibodies may be readily produced in such vertebrate system.

Both method and apparatus for the determination of the concentration of immunologically reactive biological particles in a biological sample as disclosed in U.S. Pat. No. 3,960,489 - Giaever, incorporated by reference.

The term "biological particle" is intended to encompass any material capable of stimulating antibody production when injected into an animal (i.e., an antigen) and/or having the property of interacting specifically either immunologically (i.e., a hapten) or non-immunologically.

As used herein the term "diagnostic substrate" means a substrate fabricated from a suitable material (such as metal, glass, plastic or similar material) that is nonreactive with the biological particles utilized therewith, which substrate has a first layer of biological particles adsorbed on a major surface thereof and can be used for the detection of select biological particles permitted to form a second layer over at least some part of the first layer. The construction and use of various diagnostic substrates is described in the U.S. Pat. Nos. 3,926,564 - Giaever; 3,979,184 - Giaever; 3,979,509 - Giaever; 4,011,308 - Giaever; 4,054,646 - Giaever; 4,041,146 - Giaever; and 4,090,849 - Healy et al. Diagnostic substrate configurations other than those specifically disclosed therein may be employed. The aforementioned patents are incorporated by reference.

The term "metallized" as employed herein in describing substrate constructions encompasses having a layer of metal with or without oxide content of one or more of such metals as are present in the layer. Thus, a preferred diagnostic substrate is a metallized glass slide with a layer of select biological particles adsorbed on the metallized surface area.

DESCRIPTION OF THE INVENTION

A diagnostic device is described embodying a solid, rigid diagnostic substrate (having as a part thereof an exposed layer of first, i.e., select, biological particles) in combination with means spaced therefrom for containing a solution having second biological particles. The second biological particles will specifically interact with the select particles, as for example, by immunological reaction.

The containing means is predominantly longitudinally-extending in extent and the diagnostic substrate is supported relative to the containing means so that the layer of first biological particles is adjacent to and facing the containing means, which is supported on a rigid surface. The orientation of the diagnostic substrate relative to the containing means along a line extending in the general longitudinal direction of the containing means is such that from one end of the containing means to the opposite end thereof there is constantly increasing separation between the diagnostic substrate and the containing means.

In conduct of the test, liquid containing second biological particles specific to the select biological particles for which the concentration is being determined, is absorbed into the containing means and a small volume of test liquid suspected of containing select particles is applied directly over the containing means. Typically, the test liquid will have been adjusted to increase its viscosity. Next, the diagnostic substrate is placed with the layer of specific particles thereon in contact with the test solution and with at least a portion thereof spaced from the containing means in an orientation distorting the initial shape of the deposit of test liquid and converting it into a liquid-filled zone having a constantly increasing thickness.

Initially, as the second (specific) biological particles diffuse up into the liquid-filled zone from the containing means, these second particles complex with any select particles present in the test liquid and, therefore, are unable to reach and bind to the layer of specific particles on the substrate. In time, depending on the concentration of the select particles in the test liquid, some of the second particles are able to diffuse all the way to the diagnostic substrate and complex with its exposed layer of select particles. Wherever such complexing occurs a second and visible layer is formed. Such second layer formation occurs first at the thin end of the zone of test liquid, where there is a smaller quantity of select particles separating the second particles from the diagnostic substrate. As more time is allowed for diffusion, the complexing event will proceed along the diagnostic substrate opposite thicker regions of this zone. Having defined the change in thickness of the liquid-filled zone along the longitudinal extent of the containing means, a reading of the extent (length and/or area) of the double layer formation on the diagnostic substrate provides a measure of the concentration of select particles present in the test liquid. Depending upon the diagnostic substrate employed and the method of its use the second layer may be visible with good contrast to the unaided eye or may be removed and its content so removed, or its absence, detected.

In the preferred arrangement the containing means is disposed in a generally planar orientation extending along a flat surface of the diagnostic substrate is planar and is disposed relative to the containing means such that the plane of the underside of the diagnostic substrate and the plane of the surface of the containing means define two opposite faces of a substantially wedge-shaped volume to be occupied by the test fluid. The orientation of the substrate and the containing means in this arrangement is such that a plane passed perpendicular to the diagnostic substrate and substantially parallel to the longitudinal extent of the containing means will be perpendicular to the plane of the containing means.

BRIEF DESCRIPTION OF THE DRAWING

The following portion of the description sets forth the manner and process of making and using the invention and the accompanying drawing forms part of the description for the schematic illustration thereof.

MANNER AND PROCESS OF MAKING AND USING THE INVENTION

Figure 1:
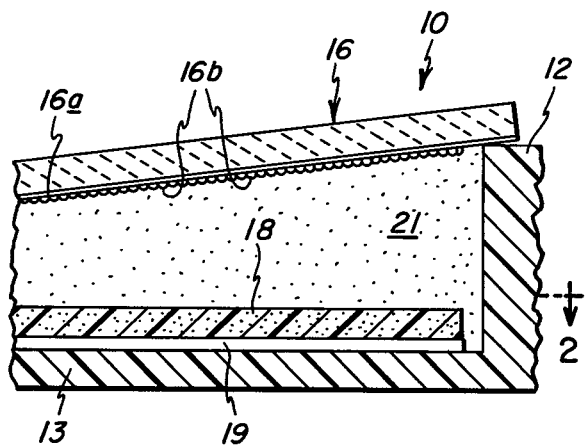
FIG. 1 shows a vertical section through the diagnostic device of this invention.

Although the device and method of this invention are broadly applicable to determining the concentration of a select biological particle in a test fluid, said select biological particle having the property of interacting specifically with another specific biological particle, the invention will be described hereinbelow in the measurement of the level of immunoglobulin IgG in human serum. The apparatus is exemplary and, for example, the diagnostic substrate need not be planar in configuration, but may be stepped or curved.

A generally channel-shaped holder 10 having spaced impermeable opposed walls 11,12 and bottom 13 having a flat upper surface serves to retain the test liquid. If desired, end walls (not shown) may also be provided. Ledge 14 is formed along wall 11 to provide support for the lower end of inclined diagnostic substrate (a glass slide having indium layer 16a thereon with adsorbed layer 16b of purified human IgG thereover) shown with the upper end thereof resting on the top of wall 12. The degree of inclination is exaggerated for ease of illustration. In the position shown a generally wedge-shaped volume is defined between slide (or diagnostic substrate) 16, wall 12, bottom 13 and vertical surface 17.

The containing means 18 is made of a suitable liquid absorbing material (i.e., porous and non-reactive), such as cellulose acetate. Preferably the containing means (or moisture holding medium) is affixed to the upper surface of bottom 13 by means of transfer adhesive tape 19 and, when viewed in plan (FIGS. 2 and 3), is formed in a convoluted or serpentine configuration affixed flat against the planar surface of bottom 13. The containing means may, for example, be readily cut or stamped from a thin sheet of cellulose acetate or cellulose. Also, the containing means may comprise a gel disposed in a recess in bottom 13.

Slide 16, when in place with its ends resting on ledge 14 and wall 12, is disposed at a slight angle to the plane of containing means 18, this angle preferably being in the range of from about 3 minutes to about 10 degrees. Although this angle providing the wedge-like definition of volume is relatively small, it is sufficient (when the test liquid, a dilution of human serum, 21 is in place) to provide significant differentiation between the extent of arrival of anti-human IgG molecules at the lower end of layer 16b as contrasted to the higher end thereof.

It is preferred that the phenomenon of transport of the anti-human IgG molecules from absorbing means 18 through the superimposed human serum 21 be by substantially pure diffusion and for this reason it may be necessary to minimize convection in the superimposed liquid. This can be done by assuring sufficiently high viscosity of the test liquid. If convection is properly reduced to a negligible amount with respect to the rate of diffusion, the reproduction on IgG layer 16b of the repeating pattern in which the absorbing means 18 has been shaped will occur as a second layer (not shown) having distinct lines. If the lines delineating the reproduction are fuzzy, a first approach is to increase the viscosity of the human serum. With aqueous solutions, appropriate increases in viscosity may be effectuated by introducing the liquid into a hydroxypropyl methyl cellulose solution or a glycerol solution. If this does not cure the problem of fuzziness, a less dilute sample is employed.

Figure 2:
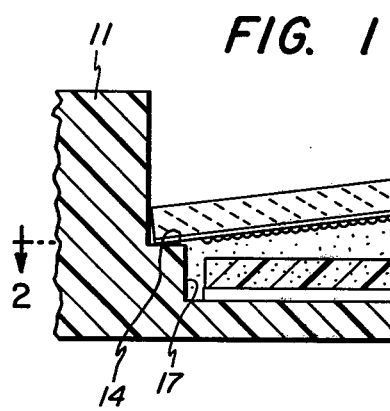
FIGS. 2 and 3 are sectional views through the device on line 2—2 to show different configurations of the containing means.
Figure 2:
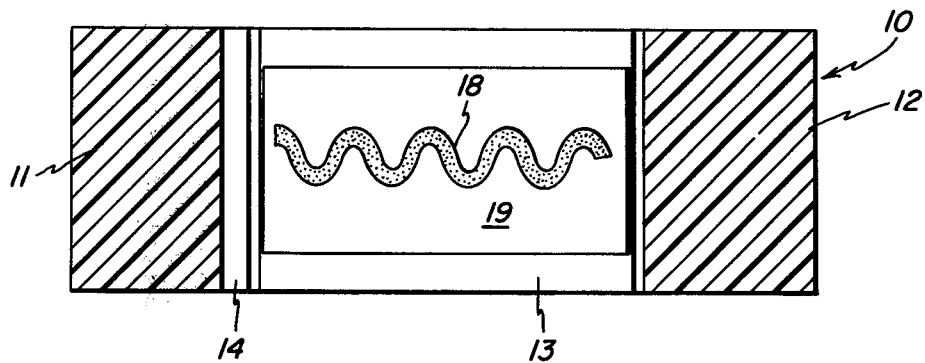
Figure 3:
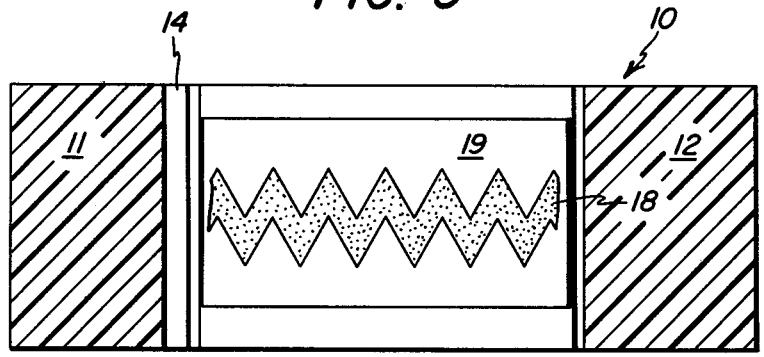

Although each of FIGS. 2 and 3 shows a single strip in place of containing means 18 cut in a repeating pattern, the number of strips may be increased as desired with each of the strips 18 receiving a different concentration of anti-human IgG serum for absorption therein. In a variant the strips 18 may receive different anti-human serums, the slide being provided with a separate strip of a particular biological particle relating to the particular strip below it. By this means simultaneous tests may be conducted for IgG, IgM and IgA, for example.

In the method of this invention, a one-step inhibition test as presently conducted, a strip of cellulose acetate paper in some desired shape is first attached with transfer tape 19 to the flat surface of bottom 13 as shown. Anti-human IgG serum is applied to paper 18 and is absorbed therein. Following adsorption, excess anti-human IgG serum is blotted away. The human serum whose IgG level is to be measured is diluted in a 1% hydroxypropyl methyl cellulose solution and a small volume of the mixture (e.g., approximately 0.2 ml) is pipetted directly on the cellulose acetate paper. Finally, slide 16 consisting of a flat piece of glass, layer 16a of indium thereon and layer 16b of purified human IgG adsorbed on indium layer 16a is placed with opposite ends thereof on ledge 14 and wall 12 and with layer 16b facing down as shown. The disposition of slide 16 in this manner repositions the human serum dilution 21 into a wedge-shaped zone, the amount of this liquid previously deposited being as much or slightly more than will fill the volume between slide 16 and the walls of device 10.

As the anti-human IgG serum diffuses from the cellulose acetate up into this liquid wedge, the specific antibodies comprising the anti-human serum complex with human IgG molecules (to the extent they are present in the test liquid 21) and are unable to proceed further toward slide 16. In time, depending on the concentration of IgG in the liquid wedge, enough free antibodies (second biological particles) are able to diffuse upwardly to IgG layer 16b where they will complex with the molecules of layer 16b and form a second, visible layer thereon. This event first occurs at the thin edge of the liquid wedge (i.e., near the lower end of slide 16) where there is less human IgG disposed between the cellulose acetate paper 18 and layer 16b of slide 16. As more time is allowed for diffusion to occur, the complexing event will gradually occur at thicker regions of the liquid wedge. After removing the slide, it is washed and dried (as by blowing).

Determining the extent (i.e., length and/or area) of the second biological particle layer formed on the diagnostic substrate is facilitated, if the cellulose acetate strip 18 is cut in a repeating pattern as, for example, is shown in FIGS. 2 and 3.

It has been found that with the construction shown in FIGS. 1 and 2 in the drawing in which ledge 14 and wall 12 are spaced one inch apart and the heights of ledge 14 and the top of wall 12 from the upper surface of bottom 13 are 0.010" and 0.020", respectively, when using a 1:100 dilution of control human serum in a 1% hydroxypropyl methyl cellulose solution, a layer of purified IgG molecules on a coating of indium, undiluted anti-human IgG (whole molecule) serum from a rabbit and a 20 minute diffusion period, the anti-human IgG layer is visible to approximately half the length of slide 16. The test conducted in this manner should reproducibly measure IgG concentrations of 0.04–0.4 mg/ml with acceptable accuracy.

If, upon conducting the test, no second layer is manifest (indicating a very high level of IgG in the patient's serum), then the test could be repeated employing a greater dilution of the liquid sample to obtain some quantitative value. If, on the contrary, for the time allotted for diffusion, the full pattern of the cellulose acetate paper is reproduced as a second layer (indicating a very low level of IgG in the patient's serum), then it will be necessary to repeat the test employing a more dilute solution of the anti-human IgG serum to obtain a quantitative value.

The concentrations of the biological particle solutions used are so selected that the range of interest of the concentrations of select biological particles will register on the slide. Usually to conduct the test a first run is made with control serum (e.g., 12 mg of IgG/ml of serum) to define what is normal and the normal range is set therefrom so that subsequent readings can be related thereto. The slide can be marked off in units for convenience in setting the range.

Variations of the device disclosed are readily contemplated as, for example, hinging slide 16 to either ledge 14 or wall 12 or using a flat holder with separate supporting means for the diagnostic substrate.

BEST MODE CONTEMPLATED

Demonstrations of this immunological test have been demonstrated in the laboratory employing a device as shown in which opposing ledge 14 and wall 12 are spaced approximately one inch apart and the heights of ledge 14 and the top of wall 12 from the upper surface of bottom 13 and 0.010" and 0.020", respectively. An IgG-coated planar indium slide and a flat-bottomed holder with a cellulose acetate strip attached thereto were employed.

What we claim as new and desire to secure by Letters Patent of the United States is:

1. Apparatus for determining the presence or absence of select biological particles in a biological sample and the concentration of said select biological particles, comprising in combination
   a solid, rigid substrate member having a layer of the select biological particles adsorbed on a major surface thereof,
   a holder comprising a solid, rigid bottom wall,
   means for containing liquid having biological particles therein specific to said select biological particles, said containing means extending along said bottom inner surface in a generally longitudinal direction, and
   means for supporting said substrate member, said supporting means holding said substrate member adjacent said containing means with at least a portion thereof spaced therefrom and with the layer of select biological particles facing said containing means, the orientation of said substrate member relative to said containing means along a line extending in the general longitudinal direction of said containing means being such that from one end of said containing means to the opposite end thereof there is constantly increasing separation between said substrate member and said containing means.

2. The apparatus of claim 1 wherein the surface of the substrate member is planar in configuration.

3. The apparatus of claim 1 wherein the surface of the containing means is planar in configuration.

4. The apparatus of claim 1 wherein the surface of the substrate member and the surface of the containing means are both planar and inclined to one another.

5. The apparatus of claim 4 wherein the inclination of the planar surfaces to each other is such that a plane passed perpendicular to the surface of the substrate member and substantially parallel to the longitudinal direction would be perpendicular to the surface of the containing means.

6. The apparatus of claim 4 wherein the angle between the plane of the substrate member and the plane of the containing means is in the range of from about 3 minutes to about 10 degrees.

7. The apparatus of claim 1 wherein the containing means is a single strip of porous material formed in a repeating pattern of relatively uniform cross-section.

8. The apparatus of claim 7 wherein the containing means is in a serpentine configuration.

9. The apparatus of claim 1 wherein the containing means is made of cellulose acetate in a substantially uniform thickness.

10. The apparatus of claim 1 wherein the containing means is affixed to the bottom inner surface.

11. The apparatus of claim 1 wherein the solid substrate member has a coating of indium upon which the layer of select biological particles is adsorbed.

12. The apparatus of claim 11 wherein the layer of select biological particles is a layer of purified human IgG.

13. The apparatus of claim 1 wherein the supporting means comprise a pair of walls in opposed relationship.

14. A method for determining the presence or absence of select biological particles in a biological sample and the concentration of said select biological particles comprising the steps of:

locating a volume of liquid containing biological particles immunologically specific to said select biological particles in a longitudinally-extending first zone, depositing a volume of sample biological liquid over said first zone in flow communication therewith, placing a layer of said select biological particles adsorbed on a solid, rigid substrate in contact with the upper surface of said sample volume so as to convert said sample volume as deposited into a second zone dimensioned to provide a constantly increasing defined change in the shortest distance through the sample liquid in said second zone from the surface of said first zone to the surface of said layer of select biological particles at succeeding stations along some line extending longitudinally along said first zone, maintaining the afore-described relationship for a preselected period of time to permit diffusion of said immunologically specific biological particles upwardly from said first zone into said second zone, removing said substrate with said layer of select biological particles adsorbed thereon, inspecting the surface of said layer of select biological particles to determine the presence and longitudinal extent of any second layer adhered to said layer of select biological particles.

15. The method of claim 14 wherein the first zone is formed by permitting the volume of liquid containing biological particles immunologically specific to the select biological particles to be absorbed by a thin layer of cellulose acetate.

16. The method of claim 14 wherein the viscosity of the sample liquid is adjusted with a substance such that convection in the liquid in the second zone is negligible with respect to the rate of diffusion of the specific biological particles from the first zone.

17. The method of claim 16 wherein the sample liquid is an aqueous solution and the substance used for viscosity adjustment is hydroxypropyl methyl cellulose.

18. The method of claim 14 wherein the liquid containing biological particles immunologically specific to the select biological particles is antihuman IgG serum, the layer of select biological particles is a layer of purified human IgG and the liquid sample is diluted human serum.

19. The method of claim 18 wherein the human serum is diluted in an aqueous hydroxypropyl methyl cellulose solution.

20. The method of claim 19 wherein twenty minutes is the time allowed for diffusion.

21. The method of claim 14 wherein the first zone has a serpentine configuration.

* * * * *